United States Patent
Saussaye et al.

(10) Patent No.: US 10,744,264 B2
(45) Date of Patent: Aug. 18, 2020

(54) AUTO-INJECTOR HAVING A MEDIAN WINDOW WITH ONE TRIANGULAR END

(71) Applicant: APTAR FRANCE SAS, Le Neubourg (FR)

(72) Inventors: Anthony Saussaye, Louviers (FR); Franck Foucault, Petit Couronne (FR); Philippe Pinheiro, Incarville (FR)

(73) Assignee: APTAR FRANCE SAS, Le Neubourg (FR)

( * ) Notice: Subject to any disclaimer, the term of this patent is extended or adjusted under 35 U.S.C. 154(b) by 87 days.

(21) Appl. No.: 15/774,631

(22) PCT Filed: Nov. 10, 2016

(86) PCT No.: PCT/FR2016/052926
§ 371 (c)(1),
(2) Date: May 9, 2018

(87) PCT Pub. No.: WO2017/081422
PCT Pub. Date: May 18, 2017

(65) Prior Publication Data
US 2018/0353692 A1 Dec. 13, 2018

(30) Foreign Application Priority Data
Nov. 13, 2015 (FR) .................................... 15 60879

(51) Int. Cl.
*A61M 5/20* (2006.01)
*A61M 5/32* (2006.01)
*A61M 5/31* (2006.01)

(52) U.S. Cl.
CPC ........ *A61M 5/2033* (2013.01); *A61M 5/3202* (2013.01); *A61M 2005/3125* (2013.01);
(Continued)

(58) Field of Classification Search
CPC .......... A61M 5/178; A61M 5/20; A61M 5/31; A61M 2205/586; A61M 2005/3125;
(Continued)

(56) References Cited

U.S. PATENT DOCUMENTS

| 2013/0079718 A1* | 3/2013 | Shang ..................... A61M 5/20 604/131 |
| 2015/0258286 A1* | 9/2015 | Mosebach ........... A61M 5/3157 604/111 |

FOREIGN PATENT DOCUMENTS

| EP | 2 716 318 A1 | 4/2014 |
| WO | 2015/036346 A1 | 3/2015 |
| WO | 2015/155482 A1 | 10/2015 |

OTHER PUBLICATIONS

International Search Report of PCT/FR2016/052926 dated Jan. 26, 2017 [PCT/ISA/210].

(Continued)

*Primary Examiner* — Jason E Flick
(74) *Attorney, Agent, or Firm* — Sughrue Mion, PLLC (57) ABSTRACT

An autoinjector having a body (1) adapted to receive a reservoir containing fluid and including a piston (P) and a needle. The body (1) has a distal portion, a middle portion, and a proximal portion, the middle portion including at least one middle window (12) making it possible, before use, to see 100% of the fluid contained in the reservoir and, after injection, to see the piston (P). The middle window (12) has an external shape of an arrow that points towards the proximal portion. The proximal portion (121) of the middle window (12) includes a triangular end portion, forming the point of the arrow, the base of the triangular end portion, remote from the point, forms the widest portion of the middle window (12).

8 Claims, 6 Drawing Sheets

(52) U.S. Cl.
CPC ... *A61M 2205/21* (2013.01); *A61M 2205/581* (2013.01); *A61M 2205/582* (2013.01); *A61M 2205/583* (2013.01)

(58) Field of Classification Search
CPC .............. A61M 5/2033; A61M 5/3202; A61M 2205/21; A61M 2205/581; A61M 2205/582; A61M 2205/583; A16M 2005/206
USPC .......................................................... 604/111
See application file for complete search history.

(56) References Cited

OTHER PUBLICATIONS

International Preliminary Report on Patentability issued from the International Bureau in counterpart International Application No. PCT/FR/2016/052926, dated Jun. 28, 2018.

* cited by examiner

AUTO-INJECTOR HAVING A MEDIAN WINDOW WITH ONE TRIANGULAR END

CROSS REFERENCE TO RELATED APPLICATIONS

This application is a National Stage of International Application No. PCT/FR2016/052926, filed Nov. 10, 2016, claiming priority based on French Patent Application No. 1560879, filed Nov. 13, 2015.

The present invention relates to an autoinjector.

Autoinjectors are well known in the prior art. The purpose of such devices is mainly to inject the contents of a syringe automatically into a patient's body. Various systems exist for making the penetration of the needle into the body of the patient and the injection of the fluid contained in the syringe automatic. Autoinjectors are relatively complex devices that must satisfy a certain number of constraint requirements in order to be reliable. The robustness of the device, its handling, and its ease of use for the user are also important elements. In addition, since most autoinjectors are for single use, the cost of manufacture and of assembly is also a factor that needs to be taken into account.

Numerous autoinjectors exist on the market, but they present a certain number of drawbacks.

Figure 1:
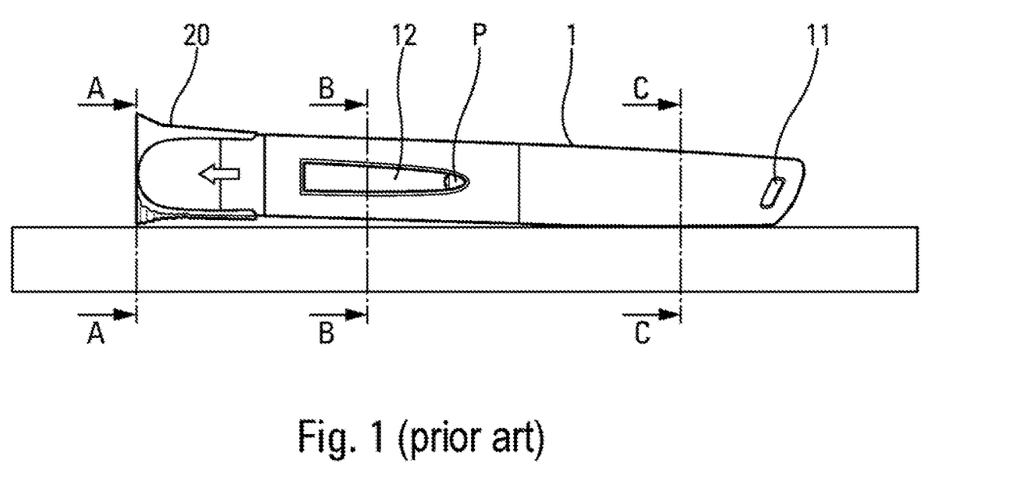
FIG. 1 is a diagrammatic side view of a prior-art autoinjector, before removal of the protective cap.
Figure 2A:
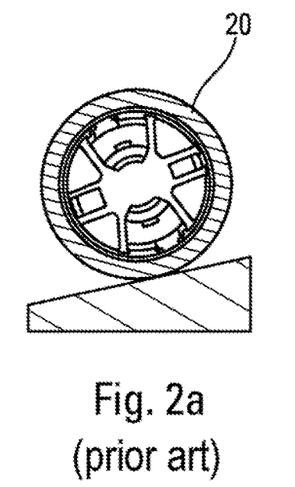
FIG. 2a is a diagrammatic section view on line A-A of FIG. 1, with the autoinjector placed on a sloping surface.
Figure 2B:
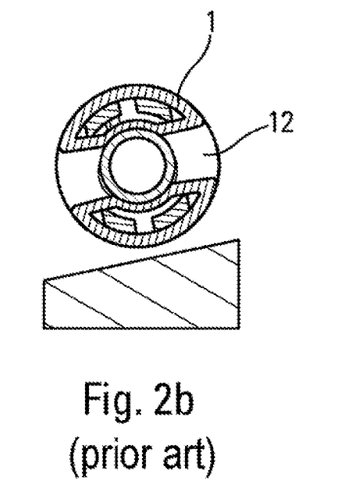
FIG. 2b is a diagrammatic section view on line B-B of FIG. 1, with the autoinjector placed on a sloping surface.
Figure 2C:
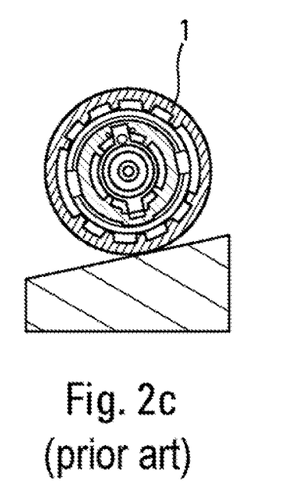
FIG. 2c is a diagrammatic section view on line C-C of FIG. 1, with the autoinjector placed on a sloping surface.
Figure 3:
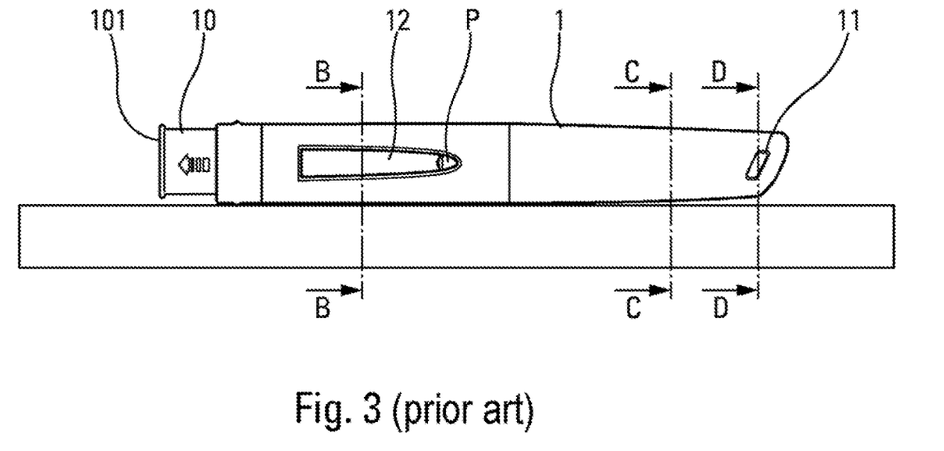
FIG. 3 is a diagrammatic side view of the FIG. 1 autoinjector, after removal of the protective cap.
Figure 4A:
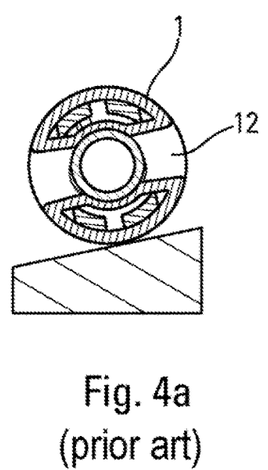
FIG. 4a is a diagrammatic section view on line B-B of FIG. 3, with the autoinjector placed on a sloping surface.
Figure 4B:
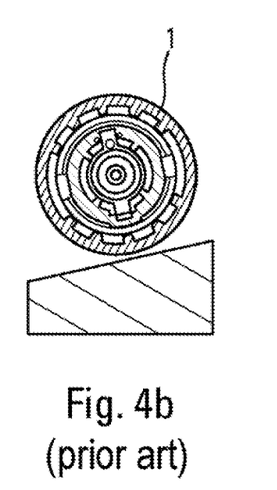
FIG. 4b is a diagrammatic section view on line C-C of FIG. 3, with the autoinjector placed on a sloping surface.
Figure 4C:
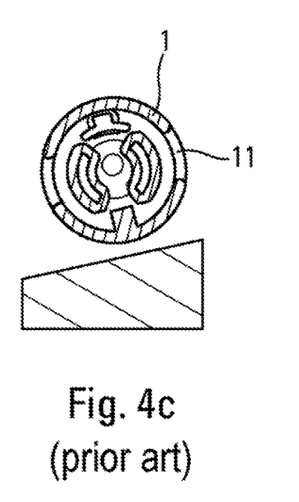
FIG. 4c is a diagrammatic section view on line D-D of FIG. 3, with the autoinjector placed on a sloping surface.

Thus, existing autoinjectors are often in the shape of an elongate cylinder. This may pose problems when the autoinjector is placed flat on a sloping surface, with the risk of the autoinjector moving by rolling about its own axis, and with a risk of the device being lost or damaged, e.g. if it falls on the floor. FIGS. 1 to 4 show this drawback. It should be observed in FIGS. 1 and 2 that while the removable cap 20 is still in place, there are two points of contact between the device and the sloping surface, namely at said cap (FIG. 2a) and at the distal portion of the body (FIG. 2c), while the middle portion is raised off said sloping surface (FIG. 2b). As a result of the circular profiles at said two points of contact, the autoinjector rolls on said sloping surface. FIGS. 3 and 4 show the situation when the removable cap 20 has been removed. It can thus be seen that only the middle portion of the body is then in contact with the sloping surface (FIG. 4a), while the proximal and distal portions (FIGS. 4b and 4c) are raised off said sloping surface. Since the profile of said middle portion is also circular, the autoinjector also rolls on said sloping surface. Thus, with or without its removable cap, the autoinjector in FIGS. 1 to 4 will not remain stationary on a sloping surface.

Another drawback with such an elongate shape may be that a user who has not been warned or who has impaired vision would risk attempting to use the autoinjector in the wrong direction, with a risk of injury by pricking by the needle and a risk of loss of dose. Thus, the FIG. 3 autoinjector, when it is used in the wrong direction, risks injuring the user with the needle, Documents EP 2 716 318, WO 2015/036346, US 2013 079718, and WO 2015/155482 describe prior-art devices.

An object of the present invention is to provide an autoinjector that does not have the above-mentioned drawbacks.

Another object of the present invention is to provide an autoinjector that is reliable in use, that is safe and that prevents any risk of injury, and that is simple and inexpensive to manufacture, to assemble, and to use.

The present invention thus provides an autoinjector comprising a body that is adapted to receive a reservoir containing fluid and including a piston and a needle, such as a pre-filled syringe, said body comprising a distal portion, a middle portion, and a proximal portion, said middle portion of said body including at least one middle window making it possible, before use, to see 100% of the fluid contained in said reservoir, and making it possible, after injection, to see said piston, said at least one middle window having an external shape in the shape of an arrow that points towards the proximal portion of said body, the proximal portion of said at least one middle window including a triangular end portion, forming the point of the arrow, the base of said triangular end portion, remote from said point, forming the widest portion of said middle window.

Advantageously, said triangular end portion is connected to the remainder of said middle window via a shoulder.

Advantageously, the distal portion of said at least one middle window includes a profile in the shape of a point that points towards said proximal portion of the body.

Advantageously, first anti-rolling means are formed by at least one radially-projecting edge of said at least one middle window.

Advantageously, said at least one radially-projecting edge surrounds said at least one middle window at least in part.

Advantageously, said middle portion of said body includes two diametrically-opposite middle windows, each including said first anti-rolling means.

Advantageously, a removable cap is fastened to said proximal portion of said body before the autoinjector is used.

Advantageously, said autoinjector includes an actuator sleeve that is movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector, said actuator sleeve being urged towards said projecting positions by a spring.

Advantageously, said actuator sleeve includes a contact end for coming into contact with the injection zone.

These characteristics and advantages and others of the present invention appear more clearly from the following detailed description, given by way of non-limiting examples, and with reference to the accompanying drawings, and in which.

In the following description, the terms "proximal" and "distal" are relative to the needle of the autoinjector. The terms "axial" and "radial" refer to the longitudinal central axis of the autoinjector. The terms "top" and "bottom" refer to the orientation in FIGS. 11a to 11d.

The autoinjector is described below with reference to advantageous embodiments. It should nevertheless be observed that autoinjectors, which are complex appliances, comprise a plurality of modules for performing a plurality of functions. The various modules may be used separately and independently of one another, without necessarily being combined with the other modules, and in particular they could be used in autoinjectors of shape that is different from the shape shown in the drawings. Furthermore, it should be observed that the drawings are diagrammatic views, which do not necessarily represent the exact shape of the components of an autoinjector, and they are not necessarily to scale, in particular for purposes of clarity. In addition, the drawings do not represent all of the component elements of an autoinjector, but only the elements necessary for operation of the present invention. Thus, the internal structures of the autoinjector, which do not affect the present invention, are not shown in the drawings for the sake of clarity, and they are described only briefly below. In addition, various additional and/or complementary elements and modules could be associated with the autoinjector shown in the figures.

The autoinjector shown in the figures comprises a body 1 in which an actuator sleeve 10 slides axially, the actuator sleeve 10 having a bottom end 101 that is for coming into contact with the body of the patient around the injection zone. Advantageously, the autoinjector may include a lower body, an intermediate body, and an upper body that are assembled together so as to form the body 1 of the autoinjector. Below, the term "body" and the numerical reference "1" are used to designate said unitary body formed by assembling said lower body with said intermediate body and said upper body. It should be observed that the body 1 could be formed of any number of body portions, e.g. two.

The body 1 includes a proximal portion, at the needle end, on which there is assembled a removable cap 20 that the user must remove before actuation. The body 1 also includes a distal portion that is axially remote from said needle and that is advantageously provided with at least one distal window 11, and a middle portion that is advantageously provided with at least one middle window 12. Said proximal, middle, and distal portions of the body 1 are advantageously of general shape that is approximately cylindrical. Likewise, the removable cap 20 advantageously has a shape that is approximately circularly cylindrical. In this variant, with or without said removable cap, the autoinjector has an elongate shape that is approximately cylindrical and that would be likely to roll when placed on a sloping plane.

A reservoir (not shown) is inserted into said autoinjector. The reservoir contains fluid and includes a piston P and a needle A. The piston P is adapted to move in said reservoir so as to inject the fluid through said needle. The present description is made with reference to a syringe that may be of any type. More generally, it is understood that the term "syringe" in the present description encompasses any type of reservoir associated with a needle. Preferably, the reservoir is a pre-filled syringe. Said reservoir can be seen through said at least one middle window 12, as shown in FIGS. 1, 3, 10, and 12. Advantageously, there are two diametrically-opposite middle windows 12 on the middle portion of the body 1. Said at least one middle window 12 makes it possible to see 100% of the liquid contained in the reservoir before use. It also makes it possible to see the piston at the end of injection. It may also show the piston before use.

The autoinjector also includes an automatic injection system, in particular comprising a piston rod (not shown) that is adapted to co-operate with the piston P so as to move it in the reservoir so as to dispense the fluid through the needle. Conventionally, the piston rod is urged by an injection spring (not shown) towards its dispensing position and, before actuation, it is held in its rest position by an appropriate injection lock. Examples of advantageous injection locks are described in particular in documents WO 2013/175148 and WO 2015/155484.

The autoinjector may also include a visual, audible, and/or tactile indicator device for indicating to the user, in particular by an audible sound, by vibration, and/or by visual and/or tactile indication, that the autoinjector may be removed from the injection site. In particular, the indicator device may include one or more indicator elements that give both a visual indication, by a suitable display in said at least one distal window 11 of the body 1, and also an audible and/or tactile indication. Advantageously, there are two diametrically-opposite distal windows 11 on the distal portion of the body 1.

Figure 7:
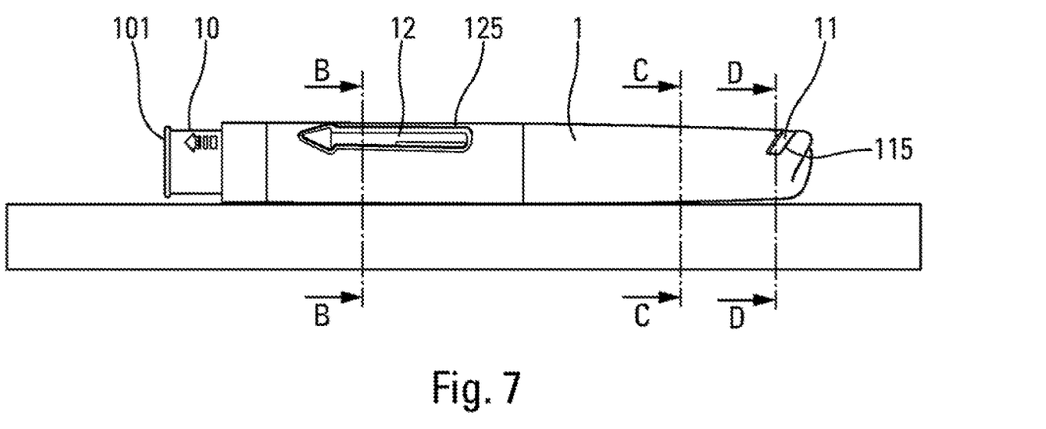
FIG. 7 is a diagrammatic side view of the FIG. 5 autoinjector, after removal of the protective cap.

The actuator sleeve 10 is urged towards its projecting positions by a spring (not shown) that may be of any type. The spring co-operates both with said actuator sleeve 10 and also with a portion that is secured to the body 1. Before actuation, the actuator sleeve 10 is in a first projecting position in which it surrounds the needle, as shown in FIG. 7. During actuation, the actuator sleeve 10 slides inside the body 1 towards an actuated position, so as to expose the needle and enable pricking, and then injection of the fluid. After injection, when the user removes the autoinjector from the injection site, the actuator sleeve 10 returns into an end-of-use second projecting position in which it is once again arranged around the needle, so as to avoid any risk of injury with said needle. It should be observed that the first and second projecting positions of the actuator sleeve 10 may be positions that are different or that are identical.

Before the autoinjector is used, the needle of the syringe is advantageously protected by a guard, typically made out of elastomer, into which the end of the needle is poked. In this configuration, removing said removable cap 20 advantageously causes said guard to be removed from the needle.

When the user wishes to use the autoinjector, the user takes hold of the device, e.g. at the body 1, and presses the actuator sleeve 10 against the part of the body where the injection is to be performed. The pressure exerted by the user on the actuator sleeve 10 causes said actuator sleeve to slide inside the body 1, thereby uncovering the needle and thus pricking the user as a result of the pressure exerted by the user on the autoinjector.

When the actuator sleeve 10 reaches its actuated position, which is its end position inside the body 1, it causes the injection stage to be triggered, during which the piston rod slides inside the syringe, pushing its piston P under the effect of the injection spring. The fluid is thus dispensed.

At the end of injection, the indicator device is actuated, possibly after a predetermined delay, so as to indicate to the user that the autoinjector may be removed from the injection site. The actuator sleeve 10 thus once again moves out from the body 1 towards the second projecting position, under the effect of its spring, with said actuator sleeve 10 being locked, and this guarantees absolute safety for the user and avoids any risk of injury with the needle after the device has been used.

In an advantageous aspect, the autoinjector may include at least two, advantageously three, anti-rolling means that prevent said autoinjector from rolling on a sloping surface, with or without removable cap 20.

Thus, said middle portion of said body 1 may include first anti-rolling means 125, forming at least one middle non-cylindrical zone in the external profile of said middle portion of said body 1. The first anti-rolling means 125 prevent any rolling after removal of the removable cap 20, as shown in FIGS. 7 and 8. It should be observed in FIG. 7 that, in the absence of the removable cap 20, the proximal and distal portions of the body 1 are not in contact with the support surface. This is shown in particular in FIGS. 8b and 8c. It is thus only the middle portion of the body 1 that is in contact with the surface, and when the surface slopes, the first anti-rolling means 125 prevent the autoinjector from rolling, as can be seen in FIG. 8a, having a right-hand portion that shows a detail of the left-hand portion on a larger scale.

Preferably, said first anti-rolling means 125 are formed by at least one projection that projects radially out from the approximately-cylindrical external profile of said middle portion of said body 1.

Figure 10A:
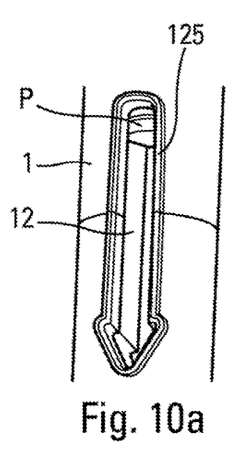
FIGS. 10a to 10d are diagrammatic side views of four variant embodiments.
Figure 10B:
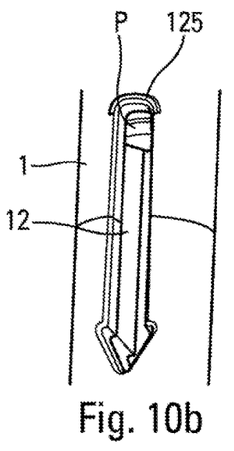
Figure 10C:
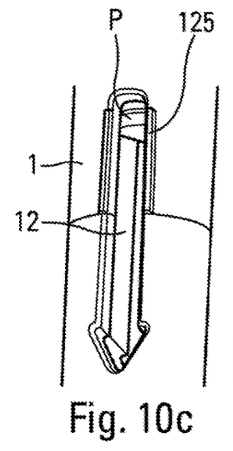
Figure 10D:
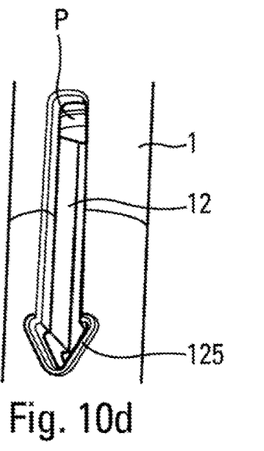

Advantageously, said first anti-rolling means 125 are formed by at least one radially-projecting edge of said at least one middle window 12. FIGS. 10a to 10d show four variant embodiments. In FIG. 10a, said radially-projecting edge surrounds said middle window 12 completely. In FIG. 10b, said radially-projecting edge surrounds only the distal portion of said middle window 12, whereas in FIGS. 10c and 10d, it is the middle and proximal portions respectively of said middle window 12 that include respective radially-projecting edges. Naturally, other variants are possible. Advantageously, two diametrically-opposite middle windows 12 are provided, each including first anti-rolling means 125.

Figure 8A:
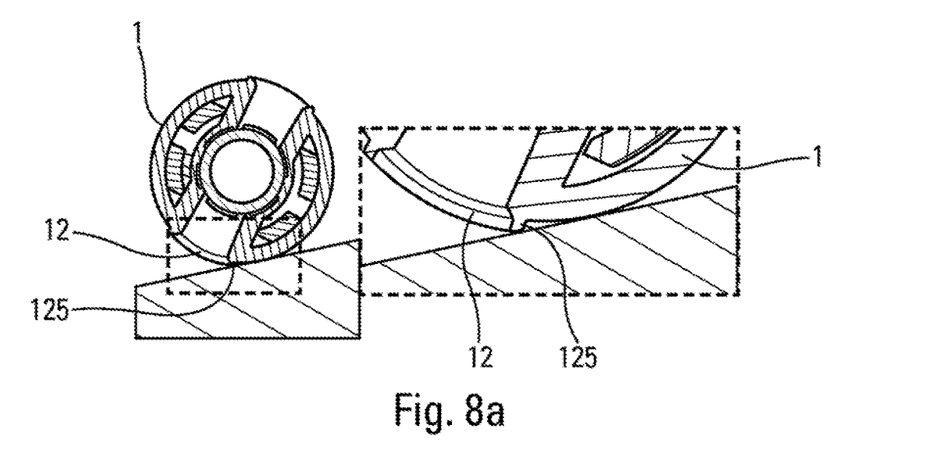
FIG. 8a is a diagrammatic section view on line B-B of FIG. 7, with the autoinjector placed on a sloping surface.
Figure 8B:
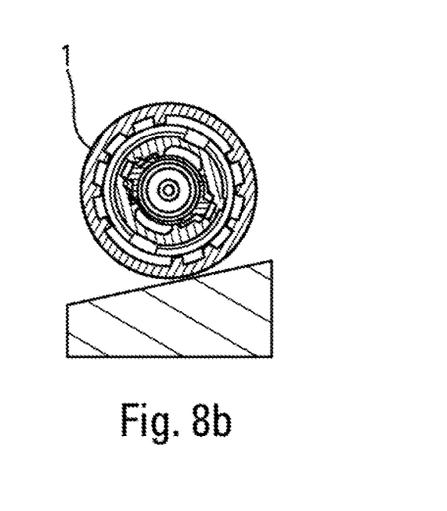
FIG. 8b is a diagrammatic section view on line C-C of FIG. 7, with the autoinjector placed on a sloping surface.
Figure 8C:
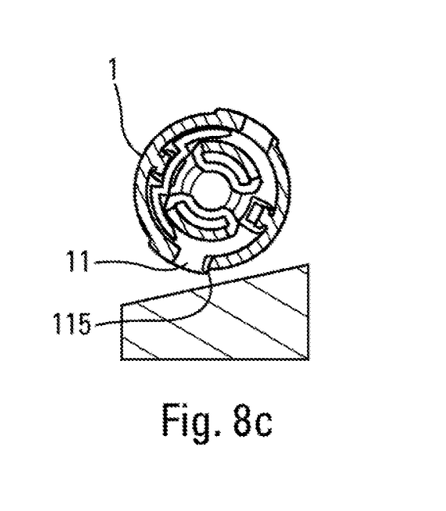
FIG. 8c is a diagrammatic section view on line D-D of FIG. 7, with the autoinjector placed on a sloping surface.

As can be seen in FIG. 8a, said radially-projecting edge forms a radial shoulder that prevents any turning of the autoinjector.

Figure 5:
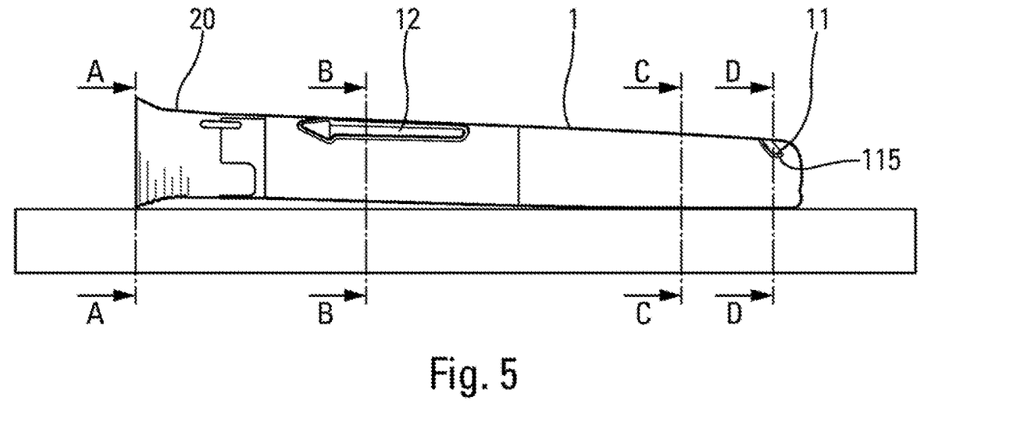
FIG. 5 is a diagrammatic side view of an autoinjector constituting an advantageous embodiment of the present invention, before removal of the protective cap.
Figure 6A:
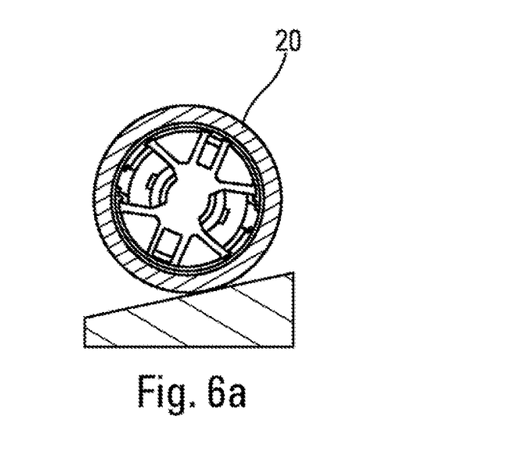
FIG. 6a is a diagrammatic section view on line A-A of FIG. 5, with the autoinjector placed on a sloping surface.
Figure 6B:
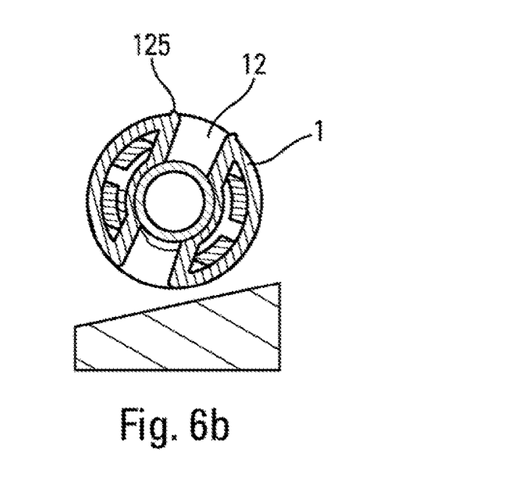
FIG. 6b is a diagrammatic section view on line B-B of FIG. 5, with the autoinjector placed on a sloping surface.
Figure 6C:
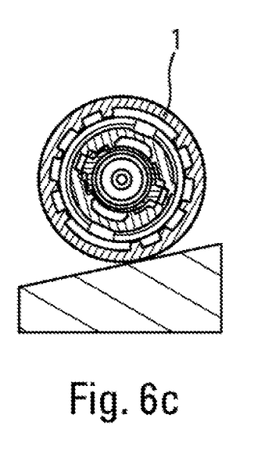
FIG. 6c is a diagrammatic section view on line C-C of FIG. 5, with the autoinjector placed on a sloping surface.

As can be seen in FIGS. 5 and 6b, said middle portion of the body 1, and in particular said middle window 12, is not in contact with the support surface when the removable cap 20 is in place. The first anti-rolling means 125 are thus not effective in this circumstance. It is thus necessary for the autoinjector to include other anti-rolling means that act when the removable cap 20 is assembled on the autoinjector.

Figure 9A:
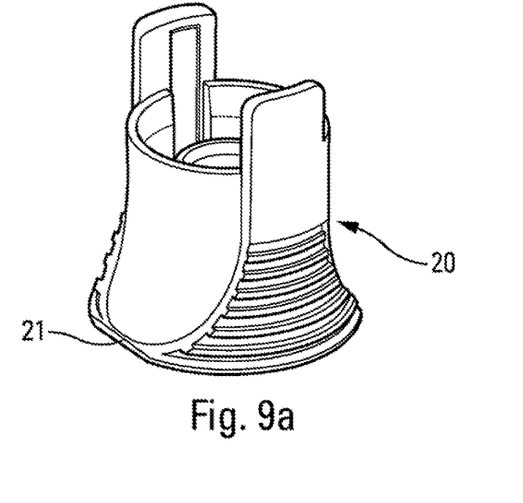
FIG. 9a is a perspective view of a removable cap in a variant embodiment.
Figure 9B:
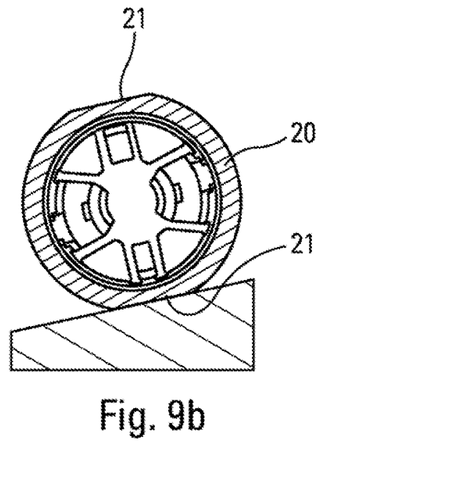
FIG. 9b is a view similar to the view in FIG. 6a, with the FIG. 9a removable cap.

In a first variant, said removable cap 20 includes second anti-rolling means 21 forming at least one proximal non-cylindrical zone in the external profile of said removable cap 20. Advantageously, said removable cap 20 includes a radially-outer portion of circular shape, said second anti-rolling means 21 being formed by at least one flat that is formed in said radially-outer portion of circular shape. This is shown in FIGS. 9a and 9b. Preferably, two diametrically-opposite flats are provided on said removable cap 20. Naturally, other variants are possible, e.g. radial projections in place of flats.

In a second variant, said distal portion of said body 1 includes third anti-rolling means 115, forming at least one distal non-cylindrical zone in the external profile of said distal portion of said body 1.

Preferably, said third anti-rolling means 115 are formed by at least one projection that projects radially out from the approximately-cylindrical external profile of said distal portion of said body 1.

Figure 11A:
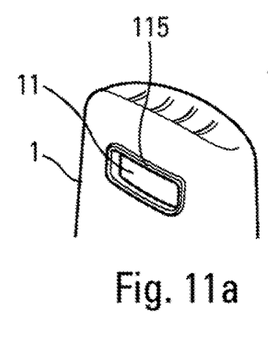
FIGS. 11a to 11d are diagrammatic side views of four other variant embodiments.
Figure 11B:
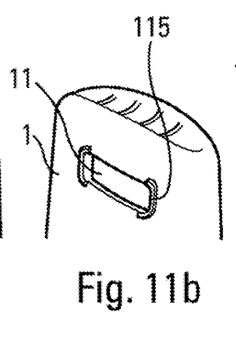
Figure 11C:
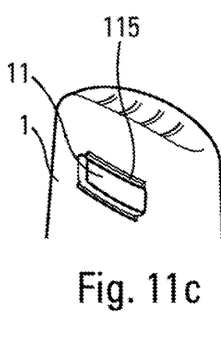
Figure 11D:
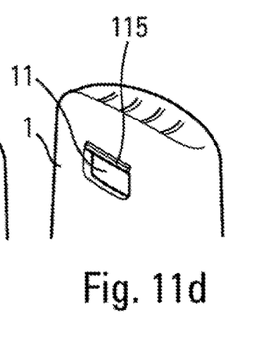

Advantageously, said third anti-rolling means 115 are formed by at least one radially-projecting edge of said at least one distal window 11. FIGS. 11a to 11d show four variant embodiments. In FIG. 11a, said radially-projecting edge surrounds said distal window 11 completely. In FIG. 11b, said radially-projecting edges are formed only on the lateral sides of said distal window 11, whereas in FIG. 11c, it is the top and bottom sides of said distal window 11 that each includes a radially-projecting edge. Finally, FIG. 11d shows a radially-projecting edge formed only on the top side of the distal window 11. Naturally, other variants are possible. Advantageously, two diametrically-opposite distal windows 11 are provided, each including third anti-rolling means 115.

Figure 6D:
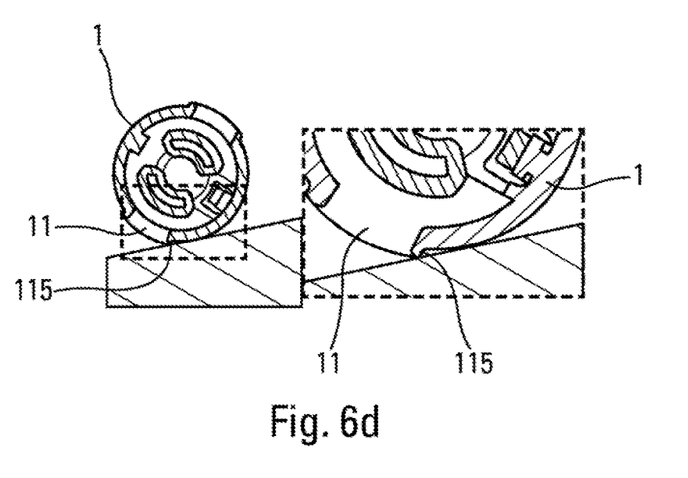
FIG. 6d is a diagrammatic section view on line D-D of FIG. 5, with the autoinjector placed on a sloping surface.

As can be seen in FIG. 6d, said radially-projecting edge forms a radial shoulder that prevents any turning of the autoinjector.

Naturally, it is possible to combine the two variants mentioned above.

In another advantageous aspect, said at least one middle window 12 has an external shape in the shape of an arrow pointing towards the proximal portion of said body 1. The purpose of this configuration is to avoid using the autoinjector in the wrong direction. The arrow shape clearly indicates to the user in which direction it is necessary to actuate the device.

Advantageously, the arrow shape can also be detected easily by people with impaired vision, in particular when said middle window 12 includes a radially-projecting edge, as described above.

In the invention, the proximal portion 121 of the middle window 12 includes a triangular end portion, forming the point of the arrow, the base of said triangular end portion, remote from said point, forming the widest portion of said middle window. This configuration makes it possible to emphasize the arrow shape of the proximal portion of the middle window 12.

FIGS. 12a to 12d show four variant embodiments.

Figure 12A:
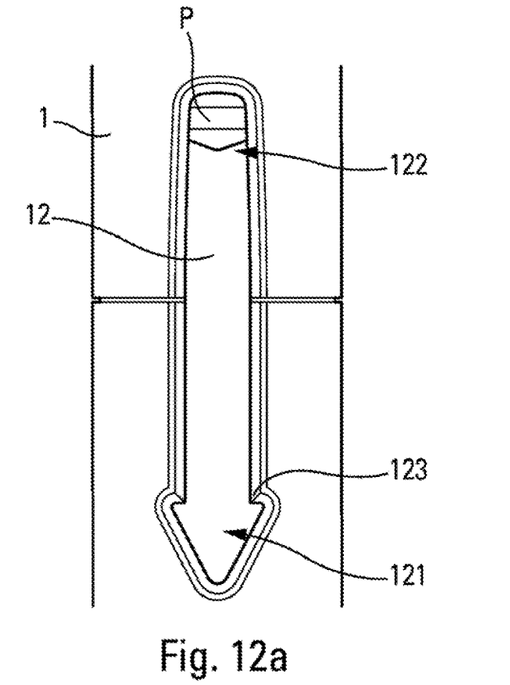
FIGS. 12a to 12d are diagrammatic side views of four other variant embodiments.
Figure 12B:
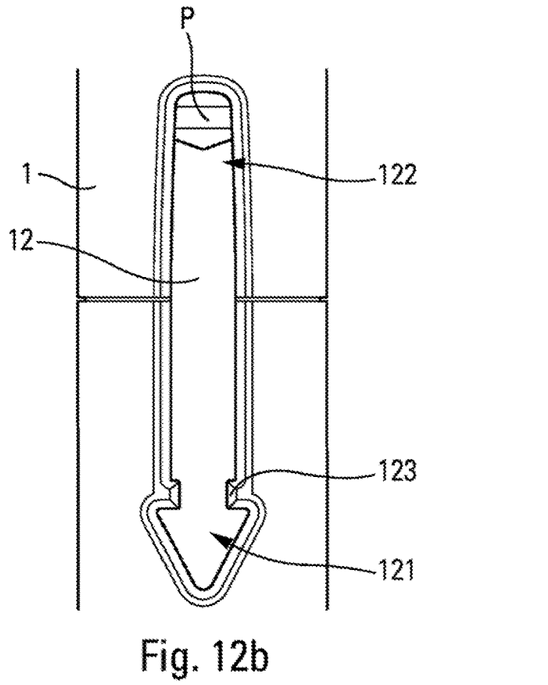

In the variants in FIGS. 12a and 12b, said triangular proximal portion 121, forming the point of the arrow, is connected to the remainder of the window via a shoulder 123. FIG. 12b includes a shoulder 123 that is larger.

Figure 12C:
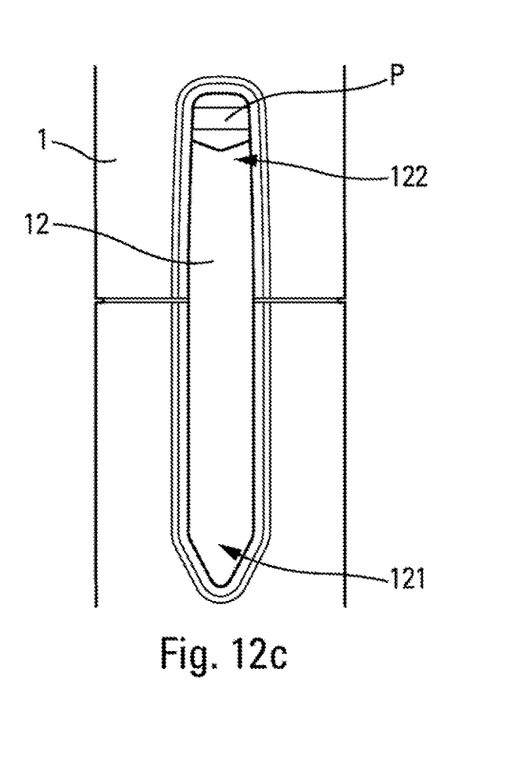

FIG. 12c also includes a triangular proximal end portion 121, but without a shoulder 123. Nevertheless, it can clearly be seen that the wide base of the point forms the widest portion of the middle window 12.

Figure 12D:
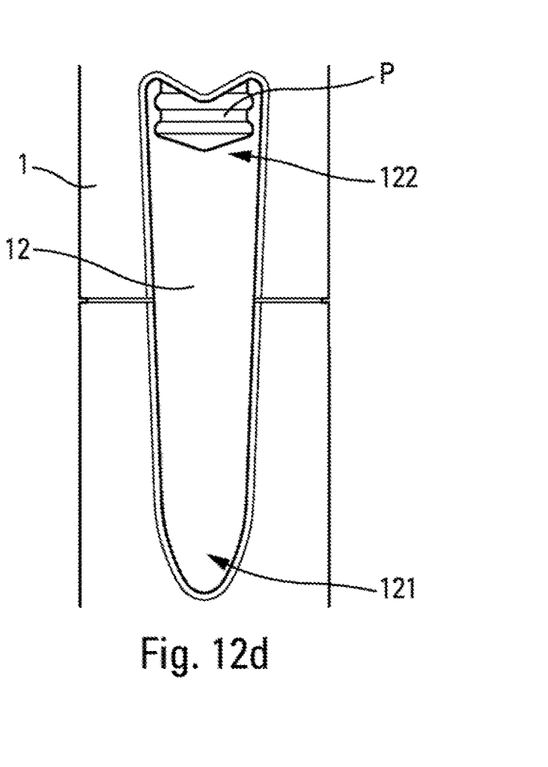

Finally, FIG. 12d includes a proximal window portion 121 that is more rounded, but that still points towards the proximal portion of the body 1. This variant of the proximal portion 121 is not covered by the present invention since the widest portion of the middle window 12 is situated at its distal portion 122. However, the variant in FIG. 12d is advantageous since it shows the distal portion 122 of the window 12, which includes a profile in the shape of a point that also points towards the proximal portion of the body 1, and this reinforces the visual impression of a middle window 12 that points towards the needle. Naturally, the distal portion 122 of FIG. 12d could be associated with the other variants of the invention in FIGS. 12a to 12c.

Naturally, other variants are possible.

The present invention applies to devices used in particular for treatment of auto-immune diseases, e.g. of the rheumatoid arthritis, multiple sclerosis, Crohn's disease type, for treatment of cancer, for antiviral treatments, e.g. of the hepatitis type, for treatment of diabetes, for treatment of anemia, or for treatment of allergy attacks, e.g. in the event of anaphylactic shock.

Although the present invention is described above with reference to advantageous embodiments, naturally various modifications can be applied thereto by the person skilled in the art, without going beyond the ambit of the present invention, as defined by the accompanying claims.

The invention claimed is:

1. An autoinjector comprising a body that is adapted to receive a reservoir containing fluid and including a piston (P) and a needle, such as a pre-filled syringe, said body comprising a distal portion, a middle portion, and a proximal portion, said middle portion of said body including at least one middle window configured, before use, to permit viewing through the middle window 100% of the fluid contained in said reservoir, and configured, after injection, to permit viewing through the middle window said piston (P), wherein said at least one middle window has an external shape in the shape of an arrow that points towards the proximal portion of said body, a proximal portion of said at least one middle window including a triangular end portion, forming the point of the arrow, a base of said triangular end portion, remote from said point, forming a widest portion of said middle window.

2. The autoinjector according to claim 1, wherein said triangular end portion is connected to a remainder of said middle window via a shoulder.

3. The autoinjector according to claim 1, wherein a distal portion of said at least one middle window forms a head of the arrow that points towards said proximal portion of the body.

4. The autoinjector according to claim 1, wherein first anti-rolling means are formed by at least one radially-projecting edge of said at least one middle window.

5. The autoinjector according to claim 4, wherein said at least one radially-projecting edge surrounds said at least one middle window at least in part.

6. The autoinjector according to claim 5, wherein said middle portion of said body includes two diametrically-opposite middle windows, each including said first anti-rolling means.

7. The autoinjector according to claim 1, wherein a removable cap is fastened to said proximal portion of said body before the autoinjector is used.

8. The autoinjector according to claim 1, comprising an actuator sleeve that includes a contact end for coming into contact with an injection zone.

* * * * *